(12) United States Patent
Moldoveanu et al.

(10) Patent No.: US 9,485,953 B2
(45) Date of Patent: Nov. 8, 2016

(54) METHOD FOR TREATING TOBACCO PLANTS WITH ENZYMES

(75) Inventors: Serban C. Moldoveanu, Winston-Salem, NC (US); Jerry Wayne Marshall, Stokesdale, NC (US); Marvin Glenn Riddick, Winston-Salem, NC (US); Michael F. Davis, Clemmons, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 1092 days.

(21) Appl. No.: 13/553,222

(22) Filed: Jul. 19, 2012

(65) Prior Publication Data
US 2014/0020694 A1    Jan. 23, 2014

(51) Int. Cl.
*A24B 15/20* (2006.01)
*A01H 5/12* (2006.01)

(52) U.S. Cl.
CPC ...................................... *A01H 5/12* (2013.01)

(58) Field of Classification Search
USPC ............ 131/41, 280, 290, 300, 352; 435/79, 435/122, 106, 135, 68.1, 101, 128, 146; 424/93.4, 94.1, 94.6
See application file for complete search history.

(56) References Cited

U.S. PATENT DOCUMENTS

| | | | |
|---|---|---|---|
| 3,132,651 A | 5/1964 | Kiefer | |
| 3,240,214 A | 3/1966 | Bayley et al. | |
| 4,140,136 A | 2/1979 | Geiss et al. | |
| 4,151,848 A | 5/1979 | Newton et al. | |
| 4,307,733 A | 12/1981 | Teng et al. | |
| 4,308,877 A | 1/1982 | Mattina | |
| 4,407,307 A | 10/1983 | Gaisch et al. | |
| 4,476,881 A | 10/1984 | Gravely et al. | |
| 4,556,073 A | 12/1985 | Gravely et al. | |
| 4,557,280 A | 12/1985 | Gravely et al. | |

(Continued)

FOREIGN PATENT DOCUMENTS

| CN | 1723811 | 1/2006 |
|---|---|---|
| CN | 102118983 | 7/2011 |

(Continued)

OTHER PUBLICATIONS

Sukhamikov et al, "Sequence, structure, and evolution of cellulases in glycoside hydrolase family 48.", J Biol Chem. Nov. 30, 2012;287(49):41068-77, [online], retrieved from the Internet, [retrieved Oct. 14, 2015], <URL: http://www.ncbi.nlm.nih.gov/pubmed/23055526>.*

(Continued)

*Primary Examiner* — Dennis Cordray
(74) *Attorney, Agent, or Firm* — Womble Carlyle Sandridge & Rice, LLP (57) ABSTRACT

A method of modifying the content of certain chemical compounds in tobacco materials is provided, the method including treatment of a tobacco plant or portion thereof with at least one enzyme. For example, the method may modify the content of tobacco smoke toxicant precursors in tobacco materials, which can result in a modification in toxicant production when the tobacco material is exposed to elevated temperatures. The type of tobacco plant or portion thereof treated according to the invention can be, for example, a tobacco seed, a tobacco seedling, an immature live plant, a mature live plant, a harvested plant, or a plant derivative. Smoking articles and other tobacco products including such enzyme-treated tobacco materials are also provided.

26 Claims, 2 Drawing Sheets

(56) References Cited

U.S. PATENT DOCUMENTS

| | | | |
|---|---|---|---|
| 4,566,469 | A | 1/1986 | Semp et al. |
| 4,716,911 | A | 1/1988 | Poulose et al. |
| 4,941,484 | A | 7/1990 | Clapp et al. |
| 5,343,879 | A | 9/1994 | Teague |
| 5,372,149 | A | 12/1994 | Roth et al. |
| 5,601,097 | A | 2/1997 | De Grandpré et al. |
| 6,298,859 | B1 | 10/2001 | Kierulff et al. |
| 6,324,785 | B1 * | 12/2001 | Marrs .................. A61K 36/185 424/773 |
| 7,132,289 | B2 * | 11/2006 | Kobayashi ............. C12M 35/02 435/458 |
| 7,393,528 | B2 | 7/2008 | Tvedten |
| 7,503,330 | B2 * | 3/2009 | Borschke ................. A24D 1/00 131/276 |
| 7,549,425 | B2 | 6/2009 | Koga et al. |
| 7,549,426 | B2 | 6/2009 | Koga et al. |
| 7,556,046 | B2 | 7/2009 | Koga et al. |
| 7,811,618 | B2 | 10/2010 | Boudreaux et al. |
| 8,105,815 | B2 | 1/2012 | Plomp et al. |
| 2011/0048434 | A1 | 3/2011 | Chen et al. |
| 2011/0155152 | A1 | 6/2011 | Harris et al. |
| 2011/0174323 | A1 | 7/2011 | Coleman, III et al. |

FOREIGN PATENT DOCUMENTS

| | | |
|---|---|---|
| EP | 1094724 | 5/2001 |
| WO | WO 00/02464 | 1/2000 |
| WO | WO 02/18607 | 3/2002 |
| WO | WO 2010/141278 | 12/2010 |
| WO | WO 2012/021683 | 2/2012 |
| WO | WO 2013/043853 | 3/2013 |

OTHER PUBLICATIONS

Liu et al., "The Use of a Novel Tobacco Treatment Process to Reduce Toxicant Yields in Cigarette Smoke," *Food and Chemical Toxicology*, 2011, vol. 49(9), pp. 1904-1917.

Boyle, "Use of Enzymes in Tobacco Manufacture," Internal Correspondence, Brown & Williamson Tobacco Corporation, Apr. 5, 1990.

Tao et al., "Review of Researches on Tobacco Quality Improvement with Enzymatic Methods," *Modern Food Science and Technology*, 2008, vol. 24, No. 7, pp. 737-741.

* cited by examiner

METHOD FOR TREATING TOBACCO PLANTS WITH ENZYMES

FIELD OF THE INVENTION

The present invention relates to plants and modifications to the method of growing, harvesting, and/or treating plants (e.g., tobacco). Particularly, the present invention relates to products made or derived from tobacco, or that otherwise incorporate tobacco, and are intended for human consumption.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are known. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; U.S. Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al; and 2011/0139164 to Mua et al.; PCT WO 04/095959 to Amarp et al. and WO 2010/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. Various types of enzymes, bacteria, and microorganisms (e.g., fungi and yeast) have been employed in conjunction with tobacco for the purpose of altering the chemical makeup of the tobacco, e.g., by reducing the content of certain chemical compounds. See, for example, U.S. Pat. No. 3,132,651 to Keifer; U.S. Pat. No. 3,513,857 to Silbeiman; U.S. Pat. No. 3,240,214 to Bayley; U.S. Pat. No. 3,636,097 to Harvey; U.S. Pat. No. 3,612,065 to Rosen; U.S. Pat. No. 3,943,945 to Rosen; U.S. Pat. No. 4,135,521 to Malan; U.S. Pat. No. 4,140,136 to Geiss et al.; U.S. Pat. No. 4,151,848 to Newton et al.; U.S. Pat. No. 4,307,733 to Teng; U.S. Pat. No. 4,308,877 to Mattina et al.; U.S. Pat. No. 4,407,307 to Gaisch; U.S. Pat. No. 4,476,881 to Gravely et al.; U.S. Pat. No. 4,556,073 to Gravely et al.; U.S. Pat. No. 4,557,280 to Gravely et al.; U.S. Pat. No. 4,566,469 to Semp et al.; U.S. Pat. No. 4,572,219 to Gaisch; U.S. Pat. No. 4,709,710 to Gaisch; U.S. Pat. No. 4,716,911 to Poulose; U.S. Pat. No. 4,887,618 to Bernasek; U.S. Pat. No. 4,941,484 to Clapp; U.S. Pat. No. 5,099,862 to White; U.S. Pat. No. 5,343,879 to Teague; U.S. Pat. No. 5,372,149 to Roth et al.; U.S. Pat. No. 5,601,097 to DeGranpreet; U.S. Pat. No. 7,549,425 to Koga et al.; U.S. Pat. No. 7,549,426 to Koga et al.; and U.S. Pat. No. 7,556,046 to Koga et al.; Int. Appl. Publ. No. WO 2000/02464 to Kierulff; and EP Appl. No. 1094724 to Kierulff, which are all incorporated herein by reference.

It would be desirable in the art to provide further methods for altering the character and nature of a plant such as a tobacco plant, as well as tobacco compositions and formulations useful in smoking articles or smokeless tobacco products.

SUMMARY OF THE INVENTION

The present invention provides a method of treating a plant or a portion thereof to modify (e.g., increase and/or decrease) the amount of certain compounds present therein and/or to provide for taste modification thereof. The plants to which the method of the invention can be applied can vary, and include without limitation any flowering plants or conifers, including various types of vines, trees, bushes, and other plants, such as those that bear fruit, vegetables, and legumes, as well as grains.

In one regard, the invention involves taking a plant that is used to produce a commodity, particularly a plant used as a source of food or other oral products, and treating the plant to modify the amount of certain compounds present in that part of the plant that is harvested. Such a method may result in the part of the plant that is harvested exhibiting certain taste changes, such as less bitterness. Certain specific plants to which the methods can be applied include, but are not limited to, vegetable plants such as beans (e.g., lima beans, green beans, soy beans, coffee beans), cabbage, okra, squash, lettuce, tomatoes, peppers, asparagus, celery, and the like; root and bulb vegetables (e.g., radishes, onions, garlic, and carrots); grains (e.g., wheat, barley, oats, corn, rice, rye, sorghum); fruit-bearing plants (e.g., strawberries); fruit-bearing vines (e.g., grapes, melons, and cranberries); fruit-bearing bushes (e.g., blueberries) and fruit-bearing trees (e.g., fruits such as oranges, lemons, limes, grapefruits, cherries, peaches, bananas, plantains, and apples); legumes (e.g., nuts); tea; hops; and herbs and spice plants. In certain embodiments, the method relates to tobacco.

In certain aspects, the invention can relate to modifying (e.g., decreasing) the content of one or more compounds in a tobacco material, comprising contacting an unharvested tobacco plant or portion thereof with one or more enzymes. In some embodiments, the unharvested tobacco plant or portion thereof is selected from the group consisting of a tobacco seed, a tobacco seedling, an immature live plant, a mature live plant, or a portion thereof.

In certain embodiments, the one or more compounds comprise smoke toxicants or smoke toxicant precursors. Exemplary smoke toxicant precursors include, but are not limited to Hoffmann analyte precursors (including, but not limited to, catechol precursors). For example, certain compounds that are advantageously modified in content in certain embodiments of to the invention are selected from the group consisting of: chlorogenic acid, rutin, proteins, amino acids, pectin, cellulose, pyridine, quinoline, 2-aminonaphthalene, 4-aminobiphenyl, hydroquinone, caffeic acid, and mixtures thereof.

In certain embodiments, the method can relate to modifying the content of certain compounds that affect the sensory characteristics of the plant (e.g., taste). Although the invention is focused on affecting the compounds present in tobacco plants, it is noted that the invention may be more generally applicable to various types of plants such as those described above. In certain embodiments, the method can relate to modifying (e.g., decreasing) amino acid content in plants that may subsequently be processed into a tobacco product, food product, or beverage product involving the application of heat (e.g., by baking, frying, or microwaving). Exemplary plants that may be processed into food products with the application of heat include, but are not limited to, cereals such as wheat and flour (e.g., for the production of breakfast cereals, biscuits, crackers, wafers, bread, crisp bread, and cookies), malt and barley (e.g., for the production of beer), potatoes (e.g., for the production of potato chips and French fries), coffee and chicory (e.g., for use in roasted coffee beverages). For example, the levels of asparagine in certain plants can be modified, which can result in an acrylamide content of the product produced therefrom that is reduced relative to an untreated product.

In some embodiments, the asparagine content of the plant or portion thereof that has been contacted with one or more enzymes according to the invention is about 50% or less by weight, about 40% or less by weight, about 30% or less by weight, or about 20% or less by weight than the asparagine content of a plant that has not been contacted with an enzyme. In other words, the plant or portion thereof (e.g., tobacco plant or portion thereof) treated according to the method of the invention can exhibit a reduction in asparagine content according to any the percentages set forth above.

The type or types of enzymes used according to the invention can vary and different enzymes can, in some embodiments, effect the modification of different compounds within the plant (e.g., the tobacco plant or portion thereof). In certain embodiments, the one or more enzymes comprise a hydrolase, isomerase, lyase, oxidoreductase, transferase, or a combination thereof. In some embodiments, the one or more enzymes comprise asparaginase. In some embodiments, the one or more enzymes comprise proteases, amylases, or a combination thereof. In some embodiments, the one or more enzymes comprise a polyphenol oxidase (e.g., a catechol oxidase).

The contacting step can, in some embodiments, comprise applying the one or more enzymes in a solution, suspension, or dispersion in water. The invention can further comprise additional steps, including, but not limited to, harvesting the unharvested tobacco plant or portion thereof and/or applying one or more probiotic bacteria, probiotic yeasts, or a combination thereof to the unharvested or harvested tobacco plant or portion thereof and/or incorporating the tobacco material into a smokeless tobacco product or a smoking article. The form of the tobacco material can, in some embodiments, be in the form of cut filler or in the form of a tobacco blend.

In some embodiments, the tobacco material is characterized by a chlorogenic acid content that is reduced relative to untreated tobacco material. For example, the amount of chlorogenic acid reduction by weight in the tobacco material can be, in some embodiments, at least about 40% relative to untreated tobacco material. In some embodiments, the tobacco material is characterized by a rutin content that is reduced relative to untreated tobacco material. For example, the amount of rutin reduction by weight in the tobacco material can be, in some embodiments, at least about 10% relative to untreated tobacco material.

In another aspect of the invention is provided a tobacco product in the form of a cigarette or a smokeless tobacco product prepared by modifying (e.g., decreasing) the content of one or more compounds in a tobacco material, comprising contacting an unharvested tobacco plant or portion thereof with one or more enzymes according to the method described herein; processing the harvested tobacco plant or portion thereof to provide a tobacco material in a form suitable for incorporation in a tobacco product; and incorporating the tobacco material into a smokeless tobacco product or a smoking article. The smoking article thus produced can be, for example, in the form of a cigarette. Accordingly, in one embodiment is provided a tobacco product in the form of a smoking article or a smokeless tobacco product, the tobacco product comprising a tobacco composition, wherein the tobacco composition comprises an enzyme-treated tobacco material.

In some embodiments, a smoking article produced from enzyme-treated tobacco material, upon smoking, is characterized by a Hoffmann analyte content of mainstream smoke that is reduced relative to an untreated control smoking article. In some embodiments, the smoking article, upon smoking, is characterized by an acrylamide content of mainstream smoke that is reduced relative to an untreated control smoking article. For example, the amount of acrylamide reduction by weight in mainstream smoke can be at least about 40% as compared to an untreated control smoking article. In some embodiments, the smoking article, upon smoking, is characterized by a catechol content of mainstream smoke that is reduced relative to an untreated control smoking article. For example, the amount of catechol reduction by weight in mainstream smoke can be at least about 5% as compared to an untreated control smoking article.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The invention provides plants, plant components, and plant materials having modified levels of certain compounds. In one exemplary aspect, the invention provides tobacco plants, plant components, or tobacco materials having modified levels of certain compounds, tobacco products incorporating tobacco material derived from such tobacco, and methods for preparing a tobacco having modified levels of certain compounds and for incorporating tobacco material derived from this tobacco within tobacco products. The method of modifying levels of certain compounds within tobacco materials generally comprises contacting tobacco (in various forms, e.g., in unharvested or harvested form) with one or more enzymes. It is noted that although the discussion provided herein focuses in large part on treatment of tobacco, a variety of other plants (including fruits, vegetables, flowers, and components thereof) can be treated according to the methods provided herein to afford plants, plant components, and materials and products produced therefrom having modified levels of certain compounds therein.

The plant or plant components can be treated with one or more enzymes in various stages of the plant life cycle. For example, the method can comprise treating an unharvested or harvested plant or plant component with one or more enzymes. The terms "plant" and "plant component" relate to a plant (e.g., a plant that produces a commodity) at any stage of the plant life cycle. The plant or plant component can be, for example, in the form of a seed, a seedling, an immature live plant, a mature live plant, a harvested plant, or a portion of any of the above (e.g., a portion of a live plant such as only the stalk or only the leaves or a portion of the surface of the seed). The commodity produced from that plant may comprise any portion of the plant (e.g., the leaf, vegetable, fruit, flower, seed, stalk, or entire plant) and thus, various portions of the plant can exhibit modified levels of certain compounds as a result of enzymatic treatment according to the methods provided herein.

In particular, in certain embodiments, the method of the invention relates specifically to enzymatic treatment of tobacco plants or portions thereof. By "tobacco," "tobacco plant," or "tobacco plant components" is meant tobacco at various stages of the tobacco plant life cycle. For example, the tobacco plant component to which the enzyme is applied can be a tobacco seed, tobacco seedling, unharvested tobacco plant (at varying stages of maturity), harvested plant, or a portion of any of the above, which are all considered to be stages of the tobacco plant as described in further detail herein. A harvested tobacco plant can be treated with one or more enzymes according to the invention in the form of, for example, an uncured (green) material, a cured/dried (e.g., air-cured or fire-cured) material, an aged material, an intact material, a cut, shredded, or ground material, an extracted material, or a tobacco extract. In certain embodiments, the tobacco is treated prior to being dried (i.e., before harvest or just after harvest). In some embodiments, the tobacco is treated in a form wherein it is considered to be "alive." In certain embodiments, the tobacco is field-treated, meaning that the enzyme or mixture thereof is applied to at least a portion of tobacco plants in unharvested form. In some embodiments, an unharvested tobacco plant to which the one or more enzymes is applied can be further described as growing in the field, having its roots in the ground, and continuing to go through the normal biological activity of a living organism.

Various enzymes and mixtures thereof can be used according to the invention. "Enzyme," as used herein, refers to any globular protein of varying size and structure. Generally, enzymes that are useful according to the invention function in some way to catalyze one or more chemical reactions within the plant material (e.g., by increasing the rate thereof). Any type of enzyme or combination of enzyme types can be employed according to the present invention; for example, hydrolases (which catalyze hydrolysis of chemical bonds), isomerases (which catalyze isomerizations within a molecule), ligases (which function to link two or more molecules), lyases (which cleave chemical bonds by mechanisms other than hydrolysis and oxidation), oxidoreductases (which catalyze oxidation/reduction reactions), and transferases (which transfer various moieties, e.g., functional groups). The origin of the enzymes can vary and the enzymes can be obtained, for example, from microbial sources (e.g., bacterial sources or fungal sources), plant sources, animal sources, and/or can be synthetically produced.

It is preferred that enzymes used according to the invention are "GRAS" (Generally Regarded as Safe), although non-GRAS enzymes can be used in certain embodiments. In certain preferred embodiments, the enzyme is an enzyme that is capable of toxicant reduction within the plant or plant component or capable of reduction of a precursor of a toxicant produced during general processing (e.g., heat treatment) or use of the plant or a component thereof.

General treatment of living plants and/or fields with enzymes for such purposes as helping to reduce stress in plants (e.g., AgPro™ Foliaraplex), stimulating plant growth and maintaining plant health (e.g., Bio-Stimulants, Verde BioScience), controlling pests (i.e., functioning as biological pesticides) (e.g., TweetMint™, Safe Solutions™, disclosed in U.S. Pat. No. 7,393,528 to Tvedten, which is incorporated herein by reference), and enhancing digestion and delivery of fertilizers and minerals in soil to plant roots (Agzyme, International Enzymes). Treatment of tobacco materials, specifically, with certain types of enzymes is known and disclosed, for example, in U.S. Pat. No. 3,132,651 to Kiefer; U.S. Pat. No. 3,240,214 to Bayley; U.S. Pat. No. 4,307,733 to Teng; U.S. Pat. No. 4,407,307 to Gaisch et al.; U.S. Pat. No. 4,716,911 to Poulose; U.S. Pat. No. 4,941,484 to Clapp et al.; U.S. Pat. No. 5,601,097 to De GrandPre et al.; U.S. Pat. No. 5,343,879 to Teague; and U.S. Pat. No. 6,298,859 to Kierulff et al.; U.S. Pat. Appl. Publ. Nos. 2011/0155152 to Harris et al and 2011/0174323 to Coleman, III et al; Int. Appl. Publ. No. WO 2000/02464 to Kierulff; EP Appl. No. 1094724 to Kierulff; and Liu et al., Food and Chem. Toxic. (2011), doi:10.1016, which are incorporated herein by reference.

According to the present invention, in some embodiments, the one or more enzymes applied to the tobacco plant or plant component comprise amylases (which catalyze the breakdown of starch into sugars) or proteases (which catalyze the hydrolysis of peptide bonds of proteins) or a combination thereof. Amylases can include α-amylase, β-amylase, γ-amylase, or a combination thereof. Proteases can include serine proteases, threonine proteases, cysteine proteases, asparatate proteases, metalloproteases, and glutamic acid proteases and certain exemplary proteases include, but are not limited to, protease *bacillus licheniformis*, protease *bacillus* sp., protease *Aspergillus oryzae*, protease *bacillus amyloliquefaciens*, protease *bacillus*, and protease *Streptomyces griseus*, which can include commercially available enzyme products Alcalase™ Esperase™, Everlase™, Flavourzyme™, Neutrase™, Protamex™, Savinase™, and Substilisin™ from Novozymes A/S In certain embodiments, the one or more enzymes comprise asparaginase (e.g., PreventASe™, DSM Food Specialties, Heerlen, NL and Acrylaway®, Novozymes, A/S, Bagsvaerd, DK). In certain embodiments, the one or more enzymes comprise a polyphenol oxidase (PPO). In some embodiments, the one or more enzymes comprise an oxidase such as a monophenol oxidase enzyme (tyrosinase) or an o-diphenol oxygen oxidoreductase enzyme (catechol oxidase). Another exemplary oxidase for use according to the invention is laccase.

According to the invention, plants or plant components can, in some embodiments, be contacted with one or more other types of reagents, either in addition to the one or more enzymes, or in place of the one or more enzymes. Exemplary reagents include amino acids (e.g., lysine, glycine, histidine, alanine, methionine, glutamic acid, aspartic acid, proline, phenylalanine, valine, and arginine), compositions incorporating di- and/or trivalent cations, certain non-reducing saccharides, certain reducing agents, phenolic compounds (e.g., compounds having at least one phenolic functionality), certain compounds having at least one free thiol group or functionality, oxidizing agents (e.g., hydrogen peroxide or ozone), oxidation catalysts (e.g., titanium dioxide), natural plant extracts (e.g., rosemary extract), and combinations thereof.

In certain embodiments, the enzymatic treatment described herein can be used in combination with probiotic treatment, as described in U.S. patent application Ser. No. 13/444,272 to Marshall et al., filed on Apr. 11, 2012, which is incorporated herein by reference. As disclosed therein, certain exemplary probiotics include, but are not limited to, *bifidobacterium adolescentis, bifidobacterium animalis, bifidobacterium bifidum, bifidobacterium breve, bifidobacterium infantis, bifidobacterium lactis, bifidobacterium longum, bifidobacterium pseudocatenulatum, bifidobacterium pseudolongum, bifidobacterium* sp., *bifidobacterium thermophilum, lactobacillus acidophilus, lactobacillus alimentarius, lactobacillus amylovorus lactobacillus bulgaricus, lactobacillus bifidus, lactobacillus brevis, lactobacillus casei, lactobacillus caucasicus, lactobacillus crispatus, lactobacillus curvatus, lactobacillus delbruckii, lactobacillus fermentum, lactobacillus gallinarum, lactobacillus gasseri, lactobacillus helveticus, lactobacillus johnsonii, lactobacillus lactis, lactobacillus leichmannii, lactobacillus paracasei, lactobacillus plantarum, lactobacillus reuteri, lactobacillus rhamnosus, lactobacillus salivarius, lactobacillus* sp., *lactobacillus sporogenes, lactococcus lactis, streptococcus cermoris, streptococcus faceium, streptococcus infantis, streptococcus thermophilus, enterococcus faceium, pediococcus acidilactici, staphylococcus thermophilus, staphylococcus camosus, staphylococcus xylosus, saccharomyces boulardii, saccharomyces cerevisiae, saccharomyces boulardii, bacillus cereus var toyo, bacillus subtilis, bacillus coagulans*, and *bacillus licheniformis*. In further embodiments, the enzyme treatment can be used in combination with treatment with one or more yeasts.

Where enzymatic treatment of a tobacco plant or plant component is used in combination with one or more additional types of treatment (e.g., treatment with amino acid, cations, saccharides, reducing agents, phenolic compounds, thiol-containing compounds, oxidizing agents, oxidation catalysts, natural plant extracts, and/or probiotics), the treatments can be performed simultaneously, in close succession, or at significantly different time points. The enzyme and one or more reagents can be incorporated within the same formulation or different formulations. In some embodiments, the enzyme and one or more reagents can be provided in separate formulations and applied at different points of the tobacco plant life cycle (e.g., with one applied to growing plants in the field and one applied following harvest or with one applied to seeds and one applied to growing plants in the field).

Enzymatic treatment of tobacco material according to the methods provided herein can have various effects on the resulting tobacco material. For example, certain enzymes are known to promote disease resistance, modify the growth of plants, modify the structure of plant cells, effect the release and/or reaction of certain compounds within the plants, among other functions. It is noted that the specific results obtained may be related, at least in part, to the specific type of enzyme or enzymes that are used in the treatment.

For example, in certain embodiments, tobacco treated with one or more enzymes exhibits modified levels of certain chemical compounds. It is believed that different enzymes can have different effects on the levels of various compounds within the tobacco. For example, amylases and proteases are known to break down starches and proteins, respectively and thus would accordingly be expected to decrease the content of certain starches and/or proteins in tobacco plants or plant components according to the present invention.

These changes can, in some embodiments, result in modification of the organoleptic properties of the tobacco, such as changes in taste or aroma (e.g., reduced bitterness or smoother flavor). Although not intending to be limited by theory, these changes can result, for example, from the decomposition of certain compounds, and/or the transformation of certain compounds within the tobacco or tobacco component. In some embodiments, the changes can result in a reduction in the amount of one or more toxicants and/or toxicant precursors (e.g., precursors to tobacco smoke toxicants) in the tobacco material. Various smoke toxicant precursors that may be advantageously reduced by enzymatic treatment according to certain aspects of the invention include, but are not limited to, structural carbohydrates such as pectin and cellulose as well as sugars, proteins and amino acids, pyridine and quinoline, acrylamide, catechol, 2-aminonapthylene, 4-aminobiphenyl, polyphenols (e.g., chlorogenic acid), rutin, and caffeic acid.

In particular embodiments, the levels of one or more amino acids and/or amino acid derivatives can be modified by enzymatic treatment as provided herein. For example, the content of asparagine, aspartic acid, and/or proline in a tobacco material can be modified by treatment of the tobacco material with an enzyme such as asparaginase (e.g., including, but not limited to, by treatment of tobacco seeds, seedlings, or live plants). Treatment of harvested tobacco with asparaginase has been discussed, for example, in US Pat. App. Publ. No. 2011/0048434 to Chen et al., which is incorporated herein by reference. In some embodiments, asparaginase treatment can result in a decrease in the asparagine content of a tobacco material and an increase in aspartic acid in that tobacco material. Although not intended to be limited by theory, it is believed that asparaginase catalyzes the hydrolysis of asparagine into aspartic acid.

Asparagine may advantageously be reduced, as asparagine is a precursor of acrylamide, which is present in cigarette smoke. By reducing the levels of asparagine in tobacco, the acrylamide level in smoke from a cigarette comprising such a tobacco can be decreased. Additionally, reducing asparagine content in tobacco used in smokeless tobacco products can reduce the amount of acrylamide produced in any heat treatment process (e.g., pasteurization) applied to the tobacco. In one embodiment, treatment of tobacco with one or more enzymes may result in an asparagine content that is less than about 50% by weight of that of an untreated tobacco, less than about 40% that of an untreated tobacco, less than about 30% that of an untreated tobacco, or less than about 20% that of an untreated tobacco. For example, an enzyme-treated tobacco material may have between about 0% and about 70% by weight, such as between about 5% and about 60%, and advantageously between about 10% and about 40% the asparagine content of an untreated tobacco material.

Correspondingly, in certain embodiments, use of an enzyme-treated tobacco can provide a smoking material that exhibits decreased acrylamide levels in the smoke produced therefrom. For example, in certain embodiments, the acrylamide level in the smoke produced from a tobacco comprising 100% enzyme-treated tobacco exhibits an acrylamide reduction of about 10% or more, about 20% or more, about 30% or more, about 40% or more, about 50% or more, about 60% or more by weight as compared with a control cigarette comprising 100% tobacco that was not enzyme-treated. Further, use of an enzyme-treated tobacco in a smokeless tobacco product can provide a product with decreased acrylamide levels. Enzyme-treated tobacco may be particularly useful in products that are heat treated at any stage of processing and/or use.

Enzyme treatment of tobacco materials can, in some embodiments, result in the modification of Hoffmann analyte and Hoffmann analyte precursor levels in tobacco. "Hoffmann analytes" refers to 44 compounds that have been noted to be constituents of smoke produced in the combustion of tobacco. The list of Hoffmann analytes includes 1-aminonaphthalene, 2-aminonaphthalene, 3-aminobiphenyl, 4-aminobiphenyl, methyl ethyl ketone, acetaldehyde, acetone, acrolein, butyraldehyde, crotonaldehyde, formaldehyde, propionaldehyde, catechol, hydroquinone, m+p-cresol, o-cresol, phenol, resorcinol, benzo[a]pyrene, ammonia, hydrogen cyanide, nitric oxide, carbon monoxide, acrylonitrile, 1,3-butadiene, benzene, isoprene, toluene, styrene, pyridine, quinoline, nicotine, arsenic, cadmium, chromium, lead, mercury, nickel, selenium, N'-nitrosoanabasine (NAB), N'-nitrosoanatabine (NAT), 4-(methylnitrosoamino)-1-(3-pyridyl)-butanone) (NNK), N'-nitrosonornicotine (NNN), and nicotine-free-dry-particulate matter. See, for example, Hoffmann, D., Hecht, S. S. Chapter 3: Advances in tobacco carcinogenesis, in Cooper, D. S., Grover, P. eds. Chemical carcinogenesis and mutagenesis. London: Springer-Verlag (1990), which is incorporated herein by reference. In certain specific embodiments, the catechol content of a tobacco material is reduced by enzymatic treatment (e.g., with a PPO or catechol oxidase).

In certain embodiments, the levels of other compounds in tobacco can be modified by treatment of the tobacco with enzymes. The decrease in these and other compounds can vary but generally, a treated tobacco will comprise between about 10% and about 90% by weight of each such compound as compared with the amount of compound present in the untreated tobacco.

Tobacco or tobaccos to which the method provided herein is applicable can vary. In certain embodiments, tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Pasado, Cubano, Jatim and Bezuki tobaccos), light air cured (e.g., North Wisconsin and Galpao tobaccos), Indian air cured, Red Russian and Rustica tobaccos, as well as various other rare or specialty tobaccos and various blends of any of the foregoing tobaccos. Descriptions of various types of tobaccos, growing practices and harvesting practices are set forth in *Tobacco Production, Chemistry and Technology*, Davis et al. (Eds.) (1999), which is incorporated herein by reference. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; U.S. Patent Appl. Pub. Nos. 2006/0037623 to Lawrence, Jr. and 2008/0245377 to Marshall et al.; each of which is incorporated herein by reference. Exemplary *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia,* and *N. spegazzinii.*

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conlding et al.; and PCT WO 2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference. Most preferably, the tobacco materials are those that have been appropriately cured and aged. Especially preferred techniques and conditions for curing flue-cured tobacco are set forth in Nestor et al., Beitrage Tabakforsch. Int., 20 (2003) 467-475 and U.S. Pat. No. 6,895,974 to Peele, which are incorporated herein by reference. Representative techniques and conditions for air curing tobacco are set forth in Roton et al., Beitrage Tabakforsch. Int., 21 (2005) 305-320 and Staaf et al., Beitrage Tabakforsch. Int., 21 (2005) 321-330, which are incorporated herein by reference. Certain types of unusual or rare tobaccos can be sun cured. Manners and methods for improving the smoking quality of Oriental tobaccos are set forth in U.S. Pat. No. 7,025,066 to Lawson et al., which is incorporated herein by reference. Representative Oriental tobaccos include katerini, prelip, komotini, xanthi and yambol tobaccos. Tobacco compositions including dark air cured tobacco are set forth in US Patent Appl. Pub. No. 2008/0245377 to Marshall et al., which is incorporated herein by reference. See also, types of tobacco as set forth, for example, in US Patent Appl. Pub. No. 2011/0247640 to Beeson et al., which is incorporated herein by reference.

The *Nicotiana* species can be selected for the content of various compounds that are present therein. For example, in certain embodiments, plants of the *Nicotiana* species (e.g., *Galpao commun* tobacco) are specifically grown for their abundance of leaf surface compounds. In certain embodiments, plants of the *Nicotiana* species are specifically grown for their relatively low levels of certain undesired compounds (e.g., asparagine). Tobacco plants can be grown in greenhouses, growth chambers, or outdoors in fields, or grown hydroponically.

The means by which enzymes can be applied to the tobacco plant can vary. Certain methods to treat plants with microorganisms which could be used, or modified for use, in the present invention are provided in U.S. Pat. No. 4,140,136 to Geiss et al.; U.S. Pat. No. 4,151,848 to Newton et al.; U.S. Pat. No. 4,308,877 to Mattina et al.; U.S. Pat. No. 4,476,881 to Gravely et al.; U.S. Pat. No. 4,556,073 to Gravely et al.; U.S. Pat. No. 4,557,280 to Gravely et al.; U.S. Pat. No. 4,566,469 to Semp et al.; U.S. Pat. No. 5,372,149 to Roth et al.; U.S. Pat. No. 7,549,425 to Koga et al.; U.S. Pat. No. 7,549,426 to Koga et al.; and U.S. Pat. No. 7,556,046 to Koga et al., all of which are incorporated herein by reference.

The method of application of enzymes as disclosed herein will often depend, at least in part, on the stage of the tobacco plant. For example, in certain embodiments, the one or more enzymes are applied to a tobacco seed prior to planting. In such embodiments, the one or more enzymes can be applied in the foini of a seed treatment or coating. For example, the seeds can be dipped in enzyme solution, soaked in enzyme solution, or sprayed with enzyme solution. In certain embodiments, the one or more enzymes are applied to a tobacco in seedling or unharvested (live) plant form or may be applied to the soil in which the tobacco plants will be planted or are presently planted. In such embodiments, spray application of enzymes can be used (e.g., using a hydraulic boom sprayer, air blast sprayer, sprinkler system, fogger, or aerial sprayer), although the method of enzyme application is not limited thereto.

Although it may be advantageous to apply the one or more enzymes while the tobacco plant is still in living form, it is also possible in some embodiments to apply certain enzymes following harvesting of the tobacco plants. Such application can occur at any time following harvest, including immediately following harvest, prior to or following post-harvest processing (e.g., drying, curing, and/or physical processing of the plant), or at any stage in between. The application of enzymes can be done at one stage in the plant life cycle, or can be conducted at two or more stages.

It can be advantageous, in some embodiments, to apply the enzymes in liquid form (e.g., as a solution, dispersion, or suspension). The liquid with which the one or more enzymes is mixed can vary, but generally, the liquid will comprise water. In some other embodiments, the one or more enzymes can be applied dry, such as in granule or dust form. The concentration and amount of the enzymes used can vary. Generally, the amount of the enzymes is an amount sufficient to change the amount of one or more compounds in the tobacco material to which it is applied.

For example, in embodiments wherein the enzyme comprises asparaginase, exemplary amounts of the enzyme can be between about 100 and about 10,000 AU per plant, e.g., between about 500 and about 5,000 AU per plant (typical AU level for a commercial product Preventase L (from DSM) is 2,600 AU/mL for the preparate of asparaginase). For dry tobacco (~12% moisture), a range between 20 and 100 AU/g can be used. In embodiments wherein the enzyme comprises commercial polyphenol oxidase (PPO), between about 100 and about 10,000 AU per plant, e.g., between about 1,000 and about 5,000 AU per plant can be used (typical AU level for a commercial product (from Worthington) is 1,000 AU/mL for the preparate).

In certain embodiments, other components can be applied to the plant with the enzymes. Such components can be added within the same formulation (e.g., solution, dispersion, suspension, or dry form) or can be applied to the tobacco in a separate formulation. For example, in some embodiments, one or more surfactants are applied to the tobacco with the enzyme or enzymes. The surfactants can be, for example, non-ionic surfactants. Various surfactants can be used, including, but not limited to, polysorbate surfactants, such as polysorbate 20 (Tween-20®) and polysorbate 80 (Tween-80®) and poly(ethylene glycol)-based surfactants, such as Triton™ X Series surfactants. Other reagents for helping the enzyme coat the tobacco effectively can include various sugars, plant extracts (e.g., yucca extracts, seaweed extracts), and derivatives thereof. Certain enzymes are active only within a particular pH range; therefore, use of pH adjusters, acids, bases, and/or buffers may be beneficial in the application of such enzymes.

The whole tobacco plant, or certain parts or portions of the plant of the *Nicotiana* species can be used and/or treated as provided herein. For example, virtually all of the plant (e.g., the whole plant) can be harvested and employed as such. Alternatively, various parts or pieces of the plant can be harvested or separated for treatment after harvest. For example, the flower, leaves, stem, stalk, roots, seeds, and various combinations thereof, can be isolated for use or further treatment.

The post-harvest processing of the plant or portion thereof can vary. After harvest, the plant, or portion thereof, can be used in a green form (e.g., the plant or portion thereof can be used without being subjected to any curing process). For example, the plant or portion thereof can be used without being subjected to significant storage, handling or processing conditions. In certain situations, it is advantageous for the plant or portion thereof be used virtually immediately after harvest. Alternatively, for example, a plant or portion thereof in green form can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

The harvested plant or portion thereof can be physically processed. The plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The tobacco material can have the form of processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina). The tobacco that is used for the tobacco product most preferably includes tobacco lamina, or a tobacco lamina and stem mixture. Portions of the tobaccos within the tobacco product may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the tobacco product optionally may incorporate tobacco that has been fermented. See, also, the types of tobacco processing techniques set forth in PCT WO 05/063060 to Atchley et al., which is incorporated herein by reference.

The manner by which the tobacco is provided in such forms can vary. The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent. Tobacco parts or pieces can be comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent.

Tobacco compositions intended to be used in a smokable or smokeless form may incorporate a single type of tobacco (e.g., in a so-called "straight grade" form). For example, the tobacco within a tobacco composition may be composed solely of flue-cured tobacco (e.g., all of the tobacco may be composed, or derived from, either flue-cured tobacco lamina or a mixture of flue-cured tobacco lamina and flue-cured tobacco stem. The tobacco within a tobacco composition also may have a so-called "blended" form. For example, the tobacco within a tobacco composition of the present invention may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other exemplary tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other exemplary tobacco blends incorporate about 20 to about 30 parts Oriental tobacco and about 70 to about 80 parts flue-cured tobacco.

Tobacco that has been treated according to the present disclosure can, in certain embodiments, be subsequently extracted. Various extraction techniques can be used. See, for example, the extraction processes described in US Pat. Appl. Pub. No. 2011/0247640 to Beeson et al., which is incorporated herein by reference. Other exemplary techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bemasek et al.;

U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

The tobacco materials discussed in the present invention can further be treated and/or processed in other ways before, after, or during the enzymatic treatment described herein. For example, if desired, the tobacco materials can be irradiated, pasteurized, or otherwise subjected to controlled heat treatment. Such treatment processes are detailed, for example, in US Pat. Pub. No. 2009/0025738 to Mua et al., which is incorporated herein by reference. It is noted that, advantageously, in some embodiments, the one or more enzymes used according to the present invention are at least about 75%, at least about 80%, at least about 85%, at least about 90%, at least about 95%, at least about 98%, at least about 99%, or completely deactivated and/or degraded at elevated temperatures. Therefore, in certain embodiment, where the enzyme-treated tobacco is heat-treated and/or used at an elevated temperature (e.g., incorporated within a cigarette, which burns at an elevated temperature), little to no active enzyme may remain in the tobacco material.

In certain embodiments, enzyme-treated tobacco materials can be further treated with water and an additive capable of inhibiting reaction of asparagine to form acrylamide upon heating of the tobacco material (e.g., an additive selected from the group consisting of lysine, glycine, histidine, alanine, methionine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof), and combinations thereof. See, for example, the types of treatment processes described in US Pat. Pub. Nos. 2010/0300463 and 2011/0048434 to Chen et al., and U.S. patent application Ser. No. 13/228,912, filed Sep. 9, 2011, which are all incorporated herein by reference. In certain embodiments, this type of treatment is useful where the original tobacco material is subjected to heat in the extraction and/or distillation process previously described. Although this type of treatment can be used in combination with the enzyme treatment of the invention, it is noted that it may not be required, as enzyme treatment can, in some embodiments, reduce acrylamide levels to a sufficiently low level on its own.

Figure 1:
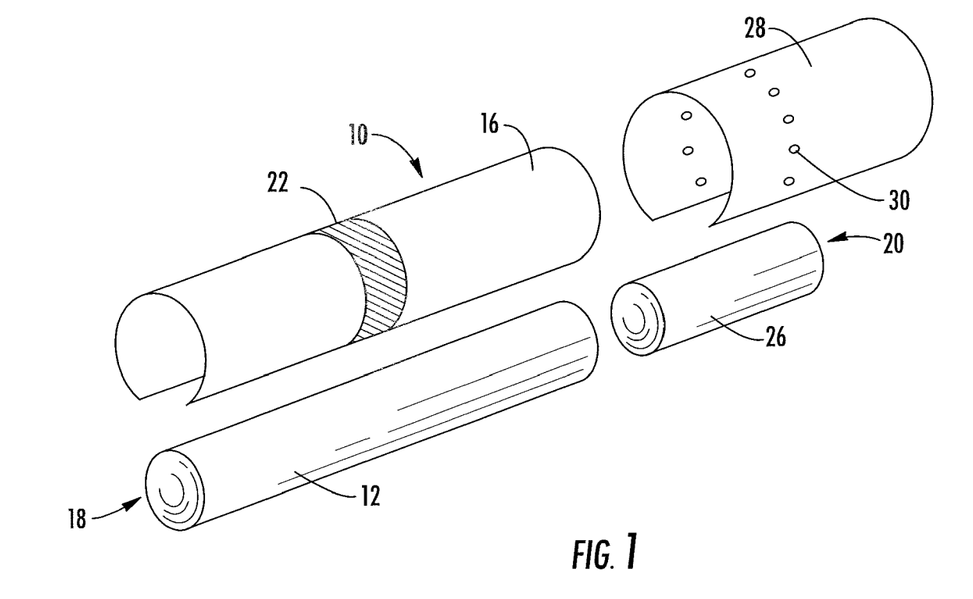
FIG. 1 is an exploded perspective view of a smoking article having the form of a cigarette, showing the smokable material, the wrapping material components, and the filter element of the cigarette.

The enzyme-treated tobacco can be incorporated within various types of tobacco products according to the present invention. For example, in some embodiments, the invention provides smoking articles, such as cigarettes, that comprise an enzyme-treated tobacco material. Referring to FIG. 1, there is shown a smoking article 10 in the form of a cigarette and possessing certain representative components of a smoking article of the present invention. The cigarette 10 includes a generally cylindrical rod 12 of a charge or roll of smokable filler material (e.g., about 0.3 to about 1.0 g of smokable filler material such as enzyme-treated tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. That is, the band 22 provides a cross-directional region relative to the longitudinal axis of the cigarette. The band 22 can be printed on the inner surface of the wrapping material (i.e., facing the smokable filler material), or less preferably, on the outer surface of the wrapping material. Although the cigarette can possess a wrapping material having one optional band, the cigarette also can possess wrapping material having further optional spaced bands numbering two, three, or more.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the plug wrap 28. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The filter element 26 is circumscribed along its outer circumference or longitudinal periphery by a layer of outer plug wrap 28. During use, the smoker lights the lighting end 18 of the cigarette 10 using a match or cigarette lighter. As such, the smokable material 12 begins to burn. The mouth end 20 of the cigarette 10 is placed in the lips of the smoker. Thermal decomposition products (e.g., components of tobacco smoke) generated by the burning smokable material 12 are drawn through the cigarette 10, through the filter element 26, and into the mouth of the smoker.

In certain embodiments, according to the invention, a smoking article comprises tobacco that has been treated with one or more enzymes. The tobacco within the smoking article can, in some embodiments, comprise only such enzyme-treated tobacco or can contain varying amounts of enzyme-treated tobacco in combination with other tobacco materials. For example, the enzyme-treated tobacco can be present in an amount of about 25% or more, about 50% or more, about 75% or more, about 80% or more, about 85% or more, about 90% or more, about 95% or more, or about 100% based on the weight of all tobacco material in the smoking article. Advantageously, in some embodiments, the one or more enzymes used in the treatment of tobacco materials is not transferred in smoke produced from a cigarette made with such tobacco.

Figure 2:
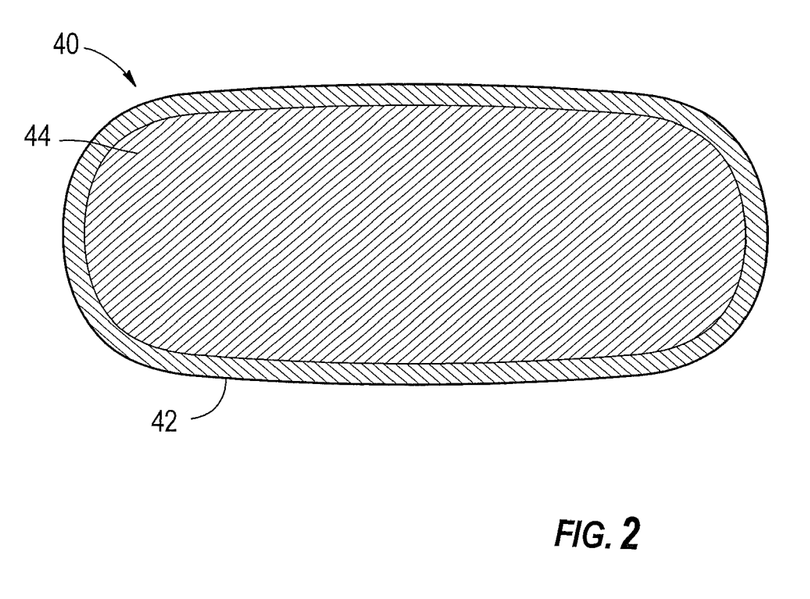
FIG. 2 is a cross-sectional view of a smokeless tobacco product embodiment, taken across the width of the product, showing an outer pouch filled with a smokeless tobacco composition of the invention.

Referring to FIG. 2, a representative snus type of tobacco product comprising the enzyme-treated tobacco of the present invention is shown. In particular, FIG. 2 illustrates a smokeless tobacco product 40 having a water-permeable outer pouch 42 containing a smokeless tobacco composition 44, wherein the tobacco composition includes a shredded or particulate tobacco material that has been treated with one or more enzymes. Further additives can be admixed with, or otherwise incorporated within, the smokeless tobacco compositions according to the invention. The additives can be artificial, or can be obtained or derived from herbal or biological sources. Exemplary types of additives include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring and titanium dioxide, and the like), humectants (e.g., glycerin, propylene glycol, and the like), oral care additives (e.g., thyme oil, eucalyptus oil, and zinc), preservatives (e.g., potassium sorbate, and the like), syrups (e.g., honey, high fructose corn syrup, and the like), disintegration aids (e.g., microcrystalline cellulose, croscarmellose sodium, crospovidone, sodium starch glycolate, pregelatinized corn starch, and the like), flavorant and flavoring mixtures, antioxidants, and mixtures thereof. If desired, the additive can be microencapsulated as set forth in US Patent Appl. Pub. No. 2008/0029110 to Dube et al., which is incorporated by reference herein. In addition, exemplary encapsulated additives are described, for example, in WO 2010/132444 A2 to Atchley, which has been previously incorporated by reference herein.

EXPERIMENTAL

The present invention is more fully illustrated by the following example, which is set forth to illustrate the present invention and is not to be construed as limiting thereof. Unless otherwise noted, all parts and percentages are by weight, and all weight percentages are expressed on a dry basis, meaning excluding water content, unless otherwise indicated.

Example

Catechol Reduction

Cut tobacco filler from commercially available Camel Blue cigarettes (R.J. Reynolds Tobacco Company) is separated from the remainder of the cigarettes. One sample of the cut tobacco filler is treated with a solution of polyphenol oxidase (PPO) enzyme. A second sample of the cut tobacco filler is treated with water to serve as a control. A third sample of the cut tobacco filler is treated with a solution of 3% hydrogen peroxide, prepared to provide an alternative method to decrease the polyphenol level in tobacco. After treatment, the cut tobacco filler samples are dried and conditioned and remade into cigarettes. The cigarettes are hand-made, further weighed, and adjusted to the same weight. The remade cigarettes are smoked in ISO conditions (see, for example, Bialous & Yach, Tobacco Control 10:96-104 (2001), which is incorporated herein by reference), and the collected particulate matter is analyzed for catechol and other phenols.

Although not intending to be limited by theory, it is believed that catechol formation originates with the pyrolysis of several precursors such as cellulose and polyphenols (e.g., chlorogenic acid and rutin). The tobacco treated with enzyme exhibits a lower polyphenol level than the untreated tobacco, as evidenced by a decrease of about 9.3% in catechol content relative to the untreated tobacco. The tobacco treated with enzyme exhibits a lower chlorogenic acid level than the untreated tobacco, as evidenced by a decrease of about 46% in chlorogenic acid content relative to the untreated tobacco. Additionally, the tobacco treated with enzyme exhibits a lower rutin level than the untreated tobacco, as evidenced by a decrease of about 16% in rutin content relative to the untreated tobacco. The tobacco treated with hydrogen peroxide solution shows virtually no difference from the untreated tobacco in both the content of polyphenols (e.g., chlorogenic acid and rutin) in the tobacco and the content of catechol in smoke produced therefrom.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of modifying the content of one or more compounds in a tobacco material, comprising contacting an unharvested tobacco plant or portion thereof with one or more enzymes, wherein the one or more enzymes comprise asparaginase.

2. The method of claim 1, wherein the unharvested tobacco plant or portion thereof is selected from the group consisting of a tobacco seed, a tobacco seedling, an immature live plant, a mature live plant, or a portion thereof.

3. The method of claim 1, wherein the contacting step comprises applying the one or more enzymes in a solution, suspension, or dispersion in water.

4. The method of claim 1, wherein the tobacco material is characterized by a reduced content of a compound selected from the group consisting of proteins, amino acids, pectin, cellulose, pyridine, quinoline, 2-aminonaphthalene, 4-aminobiphenyl, chlorogenic acid, hydroquinone, rutin, caffeic acid, asparagine, and mixtures thereof, relative to untreated tobacco material.

5. The method of claim 1, further comprising:
  harvesting the unharvested tobacco plant or portion thereof;
  processing the harvested tobacco plant or portion thereof to provide a tobacco material in a form suitable for incorporation in a tobacco product; and
  incorporating the tobacco material into a smokeless tobacco product or a smoking article.

6. The method of claim 5, wherein the tobacco material is in the form of cut filler.

7. The method of claim 5, wherein the tobacco material is in the form of a tobacco blend.

8. The method of claim 5, wherein the smoking article, upon smoking, is characterized by a Hoffmann analyte content of mainstream smoke that is reduced relative to an untreated control smoking article.

9. The method of claim 5, wherein the smoking article, upon smoking, is characterized by an acrylamide content of mainstream smoke that is reduced relative to an untreated control smoking article.

10. The method of claim 9, wherein the amount of acrylamide reduction by weight in mainstream smoke is at least about 40% as compared to an untreated control smoking article.

11. The method of claim 1, wherein the one or more compounds comprise smoke toxicants or smoke toxicant precursors.

12. The method of claim 11, wherein the one or more smoke toxicant precursors comprise Hoffmann analyte precursors.

13. The method of claim 11, wherein the one or more smoke toxicant precursors are selected from the group consisting of proteins, amino acids, pectin, cellulose, pyridine, quinoline, 2-aminonaphthalene, 4-aminobiphenyl, chlorogenic acid, hydroquinone, rutin, caffeic acid, asparagine, and mixtures thereof.

14. A method of modifying the content of one or more compounds in a tobacco material, comprising:
    contacting an unharvested tobacco plant or portion thereof with one or more enzymes,
    harvesting the unharvested tobacco plant or portion thereof; and
    applying one or more probiotic bacteria, probiotic yeasts, or a combination thereof to the unharvested or harvested tobacco plant or portion thereof.

15. The method of claim 14, wherein the one or more compounds comprise smoke toxicants or smoke toxicant precursors.

16. The method of claim 15, wherein the one or more smoke toxicant precursors comprise Hoffmann analyte precursors.

17. The method of claim 16, wherein the Hoffmann analyte precursors are catechol precursors.

18. The method of claim 15, wherein the one or more smoke toxicant precursors are selected from the group consisting of proteins, amino acids, pectin, cellulose, pyridine, quinoline, 2-aminonaphthalene, 4-aminobiphenyl, chlorogenic acid, hydroquinone, rutin, caffeic acid, asparagine, and mixtures thereof.

19. The method of claim 14, wherein the unharvested tobacco plant or portion thereof is selected from the group consisting of a tobacco seed, a tobacco seedling, an immature live plant, a mature live plant, or a portion thereof.

20. The method of claim 14, wherein the one or more enzymes comprise a hydrolase, isomerase, lyase, oxidoreductase, transferase, or a combination thereof.

21. The method of claim 14, wherein the one or more enzymes comprise proteases, amylases, or a combination thereof.

22. The method of claim 14, wherein the one or more enzymes comprise a polyphenol oxidase.

23. The method of claim 22, wherein the polyphenol oxidase comprises a catechol oxidase.

24. The method of claim 14 wherein the tobacco material is characterized by a reduced content of a compound selected from the group consisting of proteins, amino acids, pectin, cellulose, pyridine, quinoline, 2-aminonaphthalene, 4-aminobiphenyl, chlorogenic acid, hydroquinone, rutin, caffeic acid, asparagine, and mixtures thereof, relative to untreated tobacco material.

25. The method of claim 14, further comprising:
    processing the harvested tobacco plant or portion thereof to provide a tobacco material in a form suitable for incorporation in a tobacco product; and
    incorporating the tobacco material into a smokeless tobacco product or a smoking article.

26. The method of claim 25, wherein the smoking article, upon smoking, is characterized by a Hoffmann analyte content of mainstream smoke that is reduced relative to an untreated control smoking article.

* * * * *